United States Patent
Hexamer

(10) Patent No.: US 6,676,953 B2
(45) Date of Patent: Jan. 13, 2004

(54) ANTIFUNGAL COMPOSITION AND METHOD FOR HUMAN NAILS

(76) Inventor: Don L. Hexamer, 6142 Royalton Dr., Dallas, TX (US) 75230

( * ) Notice: Subject to any disclaimer, the term of this patent is extended or adjusted under 35 U.S.C. 154(b) by 0 days.

(21) Appl. No.: 09/770,336

(22) Filed: Jan. 26, 2001

(65) Prior Publication Data

US 2002/0102223 A1 Aug. 1, 2002

(51) Int. Cl.[7] .............................. A61K 6/00; A61K 7/00; A61K 7/04
(52) U.S. Cl. ........................................ 424/401; 424/61
(58) Field of Search .................................. 424/61, 401

(56) References Cited

U.S. PATENT DOCUMENTS

| | | | |
|---|---|---|---|
| 2,606,812 A | 8/1952 | Bruce | |
| 2,836,544 A | 5/1958 | Nebergall | |
| 2,882,204 A | 4/1959 | Nebergall | |
| 2,946,725 A | 7/1960 | Norris et al. | |
| 3,266,996 A | 8/1966 | Muhler | |
| 3,282,792 A | 11/1966 | Fiscella | |
| 3,346,578 A | 10/1967 | Langlykke et al. | 260/270 |
| 4,267,164 A | 5/1981 | Yeh et al. | |
| 4,335,102 A | 6/1982 | Nakashima et al. | |
| 4,459,277 A | 7/1984 | Kosti | |
| 4,599,228 A | 7/1986 | Ladanyi | |
| 4,828,822 A | 5/1989 | Muhlmann et al. | |
| 4,919,920 A * | 4/1990 | Devos | 424/61 |
| 5,057,309 A | 10/1991 | Hill et al. | 424/52 |
| 5,098,716 A | 3/1992 | Embro | |
| 5,110,809 A | 5/1992 | Wang et al. | 514/171 |
| 5,395,241 A | 3/1995 | Kandelman | 433/217.1 |
| 5,486,537 A | 1/1996 | Farinas | 514/462 |
| 5,663,208 A | 9/1997 | Martin | |
| 5,696,105 A | 12/1997 | Hackler | 514/172 |
| 5,747,070 A | 5/1998 | Majeti | |
| 5,908,640 A | 6/1999 | Embro | |
| 5,916,545 A | 6/1999 | Burnett et al. | 424/61 |
| 5,972,317 A | 10/1999 | Sorenson et al. | 424/61 |
| 5,989,522 A | 11/1999 | Friedman | |
| 6,200,553 B1 * | 3/2001 | Busch, Jr. | 424/61 |
| 6,248,370 B1 | 6/2001 | Harris | |
| 6,455,076 B1 | 9/2002 | Hahn et al. | |

* cited by examiner

Primary Examiner—Thurman K. Page
Assistant Examiner—S. Howard
(74) Attorney, Agent, or Firm—Irving M. Fishman

(57) ABSTRACT

An antifungal composition for the treatment of fungal infections in, around and under human nails, the composition comprising an aqueous solution of a wetting agent such as alcohol and a source of fluoride ions sufficient to establish a pH ranging from about 2.8 to about 3.5 in the composition. A preferred source of fluoride ions is stannous fluoride or stannous fluoride in an amount sufficient to saturate the solution. According to the method of the invention, one or more drops of the subject solution are topically applied to the infected nail and surrounding cuticular area periodically until the infection abates.

19 Claims, No Drawings

ANTIFUNGAL COMPOSITION AND METHOD FOR HUMAN NAILS

BACKGROUND OF THE INVENTION

1. Field of the Invention

This invention relates to a topical solutions and method useful for treating fungal infections of human fingernails and toenails, and for alleviating other symptoms often associated with such fungal infections.

2. Description of Related Art

Fungal infections in, under and around human fingernails and toenails can be painful, unattractive and difficult to treat. Such fungal infections, otherwise referred to as onychomycosis, ringworm of nails or tinea unguium, can cause thickening, roughness and splitting of nails. Known fungal organisms include *Epidermophyton floccusum, Trichophyton rubrum, Trichophyton mentagrophytes, Trichophyton megninii, Trichophyton schoenleinii, Trichophyton tonsurans and Candida albicans*. Although numerous systemic and topical medicaments have been disclosed previously for use in treating onychomycosis, most are ineffective, cause side effects, or are prohibitively expensive.

U.S. Pat. No. 5,916,545 discloses an antifungal composition comprising water, alcohol, a gel-forming agent and an effective amount of tioconazole, with compositions comprising from about 50 to 90 weight percent alcohol, 1 to 10 percent water, 15 to 30 percent tioconazole, 0.5 to 5 percent gel-forming agent, and a plasticizer being preferred.

U.S. Pat. No. 5,696,105 discloses a topical composition for treatment of onchomycosis comprising a therapeutically effective amount of mometasone furoate in a hydroalcoholic base comprising 15 to 50 weight percent propylene glycol, 20 to 40 percent isopropyl alcohol, 20 to 60 percent water, 0.1 to 3 percent thickening agent and sufficient buffer to adjust the pH to between 3.0 and 6.0, and most preferably between 4.0 and 5.0.

U.S. Pat. No. 5,972,317 discloses a method for treated diseased nails with a nail-permeable topical composition comprising a medicament component in combination with a proteolytic enzyme.

U.S. Pat. No. 5,486,537 discloses an antifungal composition comprising a solution of cinnamic aldehyde, up to about 20 weight percent griseofulvin and at least 5 volume percent of an alcohol selected from ethanol and isopropanol for topical application to skin and keratinous tissue.

U.S. Pat. No. 4,919,920 discloses a topical composition for hardening nails, the composition comprising a cosmetically acceptable aqueous vehicle including an effective amount of fluoride ion and having a pH of about 3.5 to 8. The fluoride ion is from a fluoride compound selected from water-soluble fluoride salts and complex fluoride salts, including aluminum fluoride, sodium fluoride, potassium fluoride, stannous fluoride, stannous monofluorophosphate, etc.

U.S. Pat. Nos. 5,395,241, 5,057,309 and 3,346,578 disclose the use of stannous fluoride in oral hygiene preparations.

SUMMARY OF THE INVENTION

Compositions useful for treating fungal infections of fingernails and toenails are desirably aqueous, fast-drying and non-greasy. Such compositions are preferably easy to apply topically, will penetrate around and under a nail, and into surrounding and underlying skin, and will desirably control or eradicate the offending fungal organisms without damaging skin or other healthy tissue.

The invention disclosed herein is an antifungal composition preferably comprising water, a wetting agent such as an alcohol, a water-soluble fluoride ion donor compound providing a concentration of fluoride ions sufficient to effectively treat a fungal infection in, on or adjacent to a human fingernail or toenail. The pH of the subject compositions preferably ranges from about 2.8 to about 3.5. The antifungal composition of the invention can desirably penetrate skin and will desirably adjust the pH on, through and under the skin to a level that is lethal to the fungal organisms without damaging the nail, skin or other surrounding tissue. A method for treating infections proximal to human nails is also disclosed that comprises periodically applying to and around an infected nail one or more drops of the subject composition for so long as the infection lasts.

DESCRIPTION OF THE PREFERRED EMBODIMENTS

The preferred compositions of the invention are made using water, a water-soluble source of fluoride ions in a concentration that is lethal to fungal organisms characteristic of onychomycosis, and a wetting agent capable of enhancing the dispersion and penetration of fluoride ions across, around and into body tissues proximal to the fungal organisms to provide and enhance contact between the fluoride ions and fungal organisms.

The invention disclosed herein is an antifungal composition comprising water, preferably a wetting agent such as an alcohol, a water-soluble fluoride ion donor compound providing a concentration of fluoride ions sufficient to effectively treat a fungal infection in, on or adjacent to a human fingernail or toenail. The subject composition can desirably penetrate skin and will desirably adjust the pH on, through and under the skin to a level that is lethal to the fungal organisms without damaging the nail, skin or other surrounding tissue. A method for treating infections proximal to human nails is also disclosed that comprises periodically applying to and around an infected nail one or more drops of the subject composition for so long as the infection lasts.

According to one preferred embodiment of the invention, an antifungal composition for the treatment of human nails and nail beds is provided that comprises a fluoride donor compound selected from the group consisting of stannous fluoride, stannic fluoride, hydrogen fluoride and dilute hydrofluoric acid. The fluoride donor compound is preferably added to a mixture of water and up to about 20 weight percent alcohol in a sufficient amount to cause the pH of the total mixture to be within a range of from about 2.8 to about 3.5. Where the fluoride donor compound is either stannous fluoride or stannic fluoride, it is believed that the amount of donor compound needed to achieve the stated pH range will dissolve in the liquid under ambient conditions. In fact, it is believed that antifungal compositions satisfactory for use in the present invention can be made by saturating the water/alcohol mixture with either stannous fluoride or stannic fluoride at ambient conditions. Any excess amount of the two compounds that is added to the water/alcohol mixture will precipitate and can be easily separated by physical separation methods well known to those of ordinary skill in the art.

Where hydrofluoric acid is used as the fluoride donor compound, care must be taken not to exceed the stated pH ranges for the antifungal composition so as to avoid injury to the user. Users should also be cautioned against leaving bottles of the solution uncovered when not in use to avoid evaporation that could increase the acidity of the composition. Well known buffering compounds can be added to the compositions of the invention to help maintain the pH within the stated preferred range.

The alcohol content of the antifungal composition of the invention, while not required, is desirably sufficient to promote movement of the composition beneath the nail and into the nail bed by capillary action. According to a preferred embodiment of the invention, the alcohol content will range up to about 20 weight percent, with about 15 to about 20 weight percent being more preferred. While methyl, ethyl and isopropyl alcohols are preferred for use in the present invention, it is believed that other alcohols, glycols and surfactants can be similarly utilized as wetting agents in the compositions of the invention in such amounts that are consistent with the other criteria of the subject compositions as disclosed herein. According to a particularly preferred embodiment of the invention, the overall antifungal composition will comprise from about 15 to about 20 weight percent isopropyl alcohol. The addition of greater amounts of alcohol can reduce the solubility of the fluoride donor compound below desirable levels.

The fluoride salts are desirably dissolved in water at concentrations approaching saturation under ambient conditions. The solutions of the invention may comprise up to about five weight percent of the fluoride ion donor compound, and solutions containing about 0.8 percent by weight of stannous fluoride ions are particularly preferred.

The wetting agent used in the solutions of the invention will desirably improve the penetration of the fluoride ions beneath the nail and into tissues in and around the nail bed, thereby promoting direct contact between the fungal organisms and the fluoride ions. The wetting agent is preferably an alcohol such as methanol, ethanol or isopropanol, although other mono-, di- and polyhydric alcohols and some glycols may also be effective for this purpose. As stated above, the amount of wetting agent in the antifungal compositions of the invention will generally range up to about 20 percent by weight of the composition.

The pH of the subject compositions is desirably such that the solution is deleterious to fungal growth without damaging the nails or surrounding tissues. Solutions having a pH ranging between about 2.8 and 3.5 are believed most suitable for the compositions of the invention. If desired, commercially available buffers can be used to facilitate control of the pH within the desired ranges.

Other optional components can also be provided for use in the compositions of the invention provided that such optional components do not unduly affect the solubilities, pH ranges and wetting ability as discussed above.

The compositions of the invention can be used as needed to prevent or control fungal growth in and around nail beds. In severe cases, initial daily topical application of the invention to the nail areas may be needed for a short period until the infection abates, with weekly applications being preferred for long term preventative or curative use. Depending upon the size of the nail and the extent of infection, one or more drops per nail may be required for each treatment.

Other alterations and modifications of the invention will likewise become apparent to those of ordinary skill in the art upon reading the present disclosure, and it is intended that the scope of the invention disclosed herein be limited only by the broadest interpretation of the appended claims to which the inventor is legally entitled.

What is claimed is:

1. A method for treating fungal growth areas proximal to a human nail, the method comprising the steps of:
   providing an aqueous solution substantially saturated with a fluorine ion donor compound and comprising up to about 20 weight percent of a wetting agent comprising an alcohol; and
   periodically topically applying the aqueous solution to the fungal growth areas.

2. The method of claim 1 wherein the fluorine donor compound is selected from the group consisting of stannous fluoride, stannic fluoride and hydrogen fluoride or dilute hydrofluoric acid.

3. The method of claim 1 wherein the wetting agent is selected from the group consisting of methanol, ethanol, and isopropanol.

4. The method of claim 1 wherein the solution comprises from about 15 to about 20 weight percent alcohol.

5. The method of claim 1 having a pH ranging from about 2.8 to about 3.5.

6. The method of claim 5 having a pH of about 2.8.

7. A method for abating fungal growth in and under skin proximal to a human nail, the method comprising the steps of:
   providing an aqueous solution that is deleterious to fungal growth without damaging nails or surrounding tissues, said solution being substantially saturated with a fluorine ion donor compound; and
   periodically topically applying the aqueous solution to the fungal growth areas until such fungal growth abates.

8. The method of claim 7 wherein the aqueous solution further comprises up to 20 weight percent of a wetting agent.

9. The method of claim 8 wherein the wetting agent is selected from the group consisting of alcohols, glycols, and surfactants.

10. The method of claim 7 wherein the pH of the aqueous solution ranges between about 2.8 and about 3.5.

11. An antifungal composition for the treatment of a fungal infection of a member selected from the group consisting of the nails, tissue surrounding said nails, and tissue underlying said nails, or treatment of symptoms associated with said fungal infection in an animal in need of said treatment comprising:
    water;
    an effective antifungal amount of a topical pharmaceutically acceptable fluoride ion donor compound; and
    an effective amount of at least one monohydric alcohol wetting agent;
    said composition being at least substantially saturated with said fluoride ion donor, and whereby when said composition is applied to said nail, or said tissue surrounding said nail or said tissue underlying said nail, said composition penetrates around and under said nail and into underlying and surrounding tissues so that said fungal infection or symptoms associated therewith are effectively ameliorated.

12. The composition of claim 11 wherein said composition is saturated with said fluoride ion donor compound.

13. The composition of claim 11 further comprising a topically acceptable buffer.

14. The composition of claim 11 wherein said composition has a pH in the range of about 2.8 to about 3.5.

15. The composition of claim 11 wherein said monohydric alcohol is selected from methanol, ethanol, and isopropanol.

16. The composition of claim 11 wherein said wetting agent is present up to an amount of 20% based on the total composition.

17. The composition of claim 17 wherein said wetting agent is present in an amount of about 15% to about 20% based on the total composition.

18. A method of treating a fungal infection of a nail or the tissue surrounding or underlying said nail or treating symptoms associated with such an infection in an animal in need thereof, comprising:

applying the composition of claim 1 to said nail or tissue surrounding or underlying said nail.

19. The method of claim 18 wherein said applying step is done on a periodic basis until said fungal infection abates.

* * * * *